United States Patent
An et al.

(10) Patent No.: US 11,760,799 B2
(45) Date of Patent: Sep. 19, 2023

(54) LEPTIN ANTIBODIES

(71) Applicant: Board of Regents, The University of Texas System, Austin, TX (US)

(72) Inventors: Zhiqiang An, Dallas, TX (US); Ningyan Zhang, Dallas, TX (US); Philipp E. Scherer, Dallas, TX (US); Shangang Zhao, Dallas, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 17/124,481

(22) Filed: Dec. 16, 2020

(65) Prior Publication Data

US 2021/0188970 A1    Jun. 24, 2021

Related U.S. Application Data

(63) Continuation of application No. PCT/US2019/037236, filed on Jun. 14, 2019.

(60) Provisional application No. 62/685,997, filed on Jun. 16, 2018.

(51) Int. Cl.
| | |
|---|---|
| *A61K 39/395* | (2006.01) |
| *C07K 16/26* | (2006.01) |
| *A61P 3/04* | (2006.01) |
| *A61K 39/00* | (2006.01) |

(52) U.S. Cl.
CPC ............... *C07K 16/26* (2013.01); *A61P 3/04* (2018.01); *A61K 2039/505* (2013.01); *C07K 2317/24* (2013.01); *C07K 2317/76* (2013.01); *C07K 2317/92* (2013.01)

(58) Field of Classification Search
None
See application file for complete search history.

(56) References Cited

PUBLICATIONS

Mahmoudian et al. Hybridoma 31(5): 372-377, 2012.*
Obradovic et al. Front. In Endocrinol. 12: 1-14, 2021.*
Izquierdo et al. Nutrients 11: 1-11, 2019.*
Izquierdo et al. (Nutrients 2019, 11, 2704; doi:10.3390/nu11112704).*
Martinez (Proc. Nutr. Soc. 59: 337-345, 2000).*
Kanasaki et al. (J. Biomed. Biotech. Volum 2011, Article ID 197636, 11 pages, 2011).*
Korner et al. N. Engl. J. Med. 349(10): 926-928, 2003.*
Science 280: 1363-1387, 1998.*

* cited by examiner

*Primary Examiner* — Christine J Saoud
(74) *Attorney, Agent, or Firm* — Richard Aron Osman

(57) ABSTRACT

Antibody antigen binding domains which specifically binds human leptin comprises $V_H$ or $V_L$ CDR1, CDR2 and CDR3 sequences of an hLept antibody. The antibody antigen binding domains and antibodies thereof are useful to treat obesity and diabetes.

4 Claims, 1 Drawing Sheet
Specification includes a Sequence Listing.

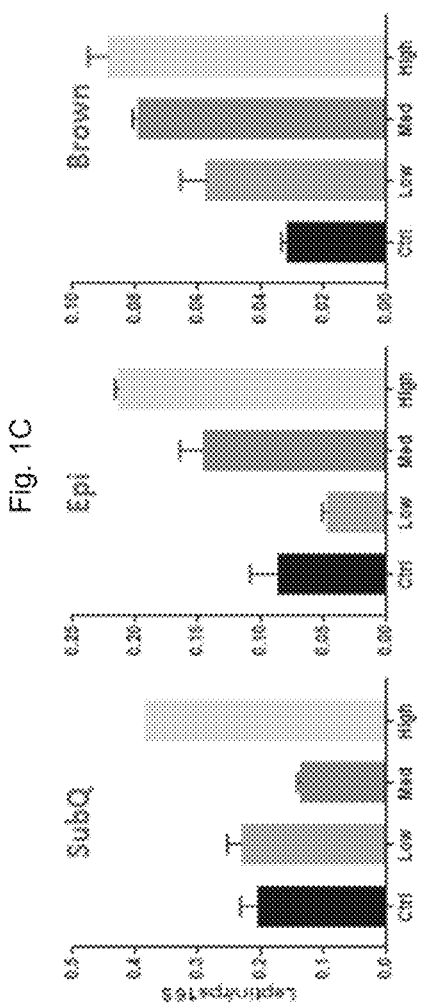
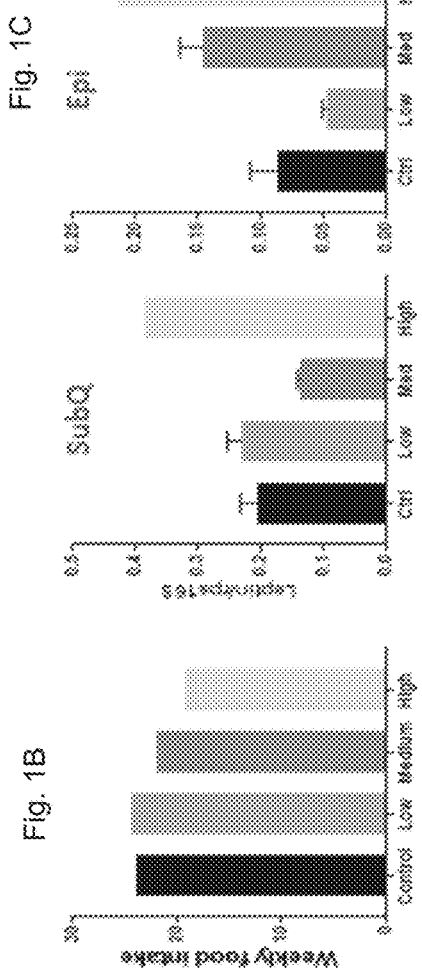
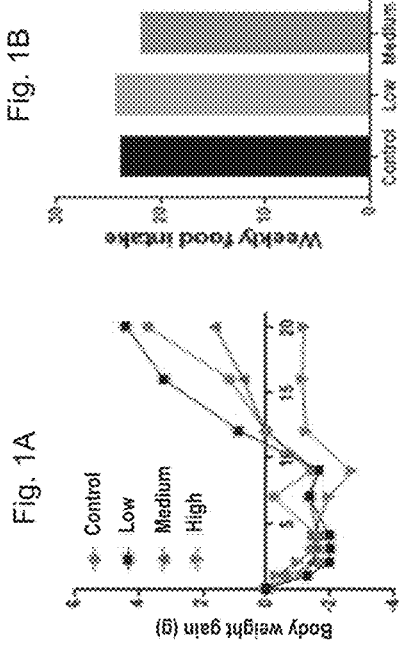
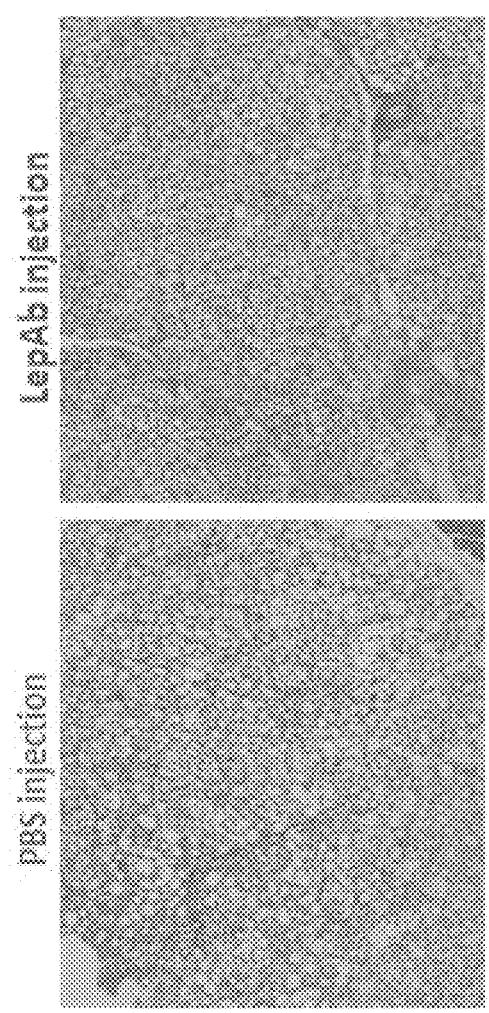
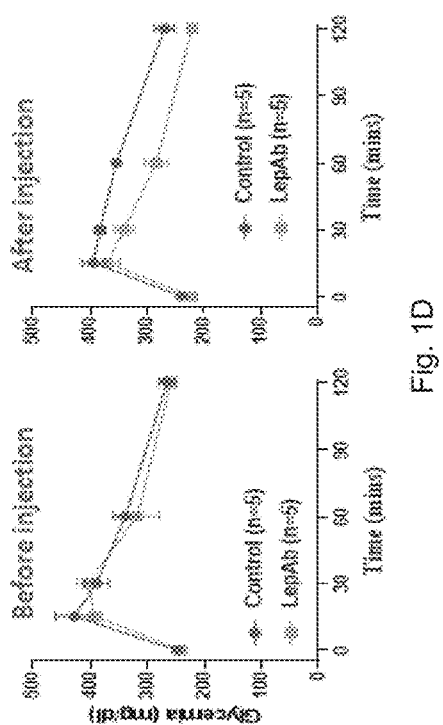

SEQUENCE LISTING

<160> NUMBER OF SEQ ID NOS: 70

<210> SEQ ID NO 1
<211> LENGTH: 10
<212> TYPE: PRT
<213> ORGANISM: Homo sapiens

<400> SEQUENCE: 1

Gly Gly Ser Val Ser Arg Gly Ser His Tyr
1               5                   10

<210> SEQ ID NO 2
<211> LENGTH: 7
<212> TYPE: PRT
<213> ORGANISM: Homo sapiens

<400> SEQUENCE: 2

Ile His Thr Asp Gly Ser Thr
1               5

<210> SEQ ID NO 3
<211> LENGTH: 10
<212> TYPE: PRT
<213> ORGANISM: Homo sapiens

<400> SEQUENCE: 3

Ala Arg Glu Pro Gly Gly Ala Leu Asn Phe
1               5                   10

<210> SEQ ID NO 4
<211> LENGTH: 8
<212> TYPE: PRT
<213> ORGANISM: Homo sapiens

<400> SEQUENCE: 4

Gly Tyr Thr Phe Thr Gly Tyr Tyr
1               5

<210> SEQ ID NO 5
<211> LENGTH: 8
<212> TYPE: PRT
<213> ORGANISM: Homo sapiens

```
<400> SEQUENCE: 5

Ile Asn Pro Asn Ser Gly Gly Thr
1               5

<210> SEQ ID NO 6
<211> LENGTH: 19
<212> TYPE: PRT
<213> ORGANISM: Homo sapiens

<400> SEQUENCE: 6

Ala Ser Gly Lys Thr Tyr Tyr Asp Phe Trp Ser Gly Arg Arg Gly
1               5                   10                  15

Met Asp Val

<210> SEQ ID NO 7
<211> LENGTH: 8
<212> TYPE: PRT
<213> ORGANISM: Homo sapiens

<400> SEQUENCE: 7

Gly Gly Thr Phe Ser Ser Tyr Ala
1               5

<210> SEQ ID NO 8
<211> LENGTH: 8
<212> TYPE: PRT
<213> ORGANISM: Homo sapiens

<400> SEQUENCE: 8

Ile Ile Pro Ile Phe Gly Thr Ala
1               5

<210> SEQ ID NO 9
<211> LENGTH: 15
<212> TYPE: PRT
<213> ORGANISM: Homo sapiens

<400> SEQUENCE: 9

Ala Arg Ser Gln Val Pro Ser Ser Tyr Tyr Tyr Gly Met Asp Val
1               5                   10                  15

<210> SEQ ID NO 10
<211> LENGTH: 8
<212> TYPE: PRT
<213> ORGANISM: Homo sapiens

<400> SEQUENCE: 10

Gly Phe Thr Phe Ser Ser Tyr Ala
1               5

<210> SEQ ID NO 11
<211> LENGTH: 8
<212> TYPE: PRT
<213> ORGANISM: Homo sapiens

<400> SEQUENCE: 11

Ile Ser Tyr Asp Gly Ser Asn Lys
1               5

<210> SEQ ID NO 12
<211> LENGTH: 12
<212> TYPE: PRT
<213> ORGANISM: Homo sapiens
```

<400> SEQUENCE: 12

Ala Arg Gly Arg Glu Tyr Tyr Tyr Tyr Met Asp Val
1               5                   10

<210> SEQ ID NO 13
<211> LENGTH: 8
<212> TYPE: PRT
<213> ORGANISM: Homo sapiens

<400> SEQUENCE: 13

Gly Tyr Thr Phe Thr Ser Tyr Tyr
1               5

<210> SEQ ID NO 14
<211> LENGTH: 8
<212> TYPE: PRT
<213> ORGANISM: Homo sapiens

<400> SEQUENCE: 14

Ile Asn Pro Ser Gly Gly Ser Thr
1               5

<210> SEQ ID NO 15
<211> LENGTH: 13
<212> TYPE: PRT
<213> ORGANISM: Homo sapiens

<400> SEQUENCE: 15

Ala Arg Gly Phe Gly Tyr Gly Gly Lys Ala Leu Asp Tyr
1               5                   10

<210> SEQ ID NO 16
<211> LENGTH: 8
<212> TYPE: PRT
<213> ORGANISM: Homo sapiens

<400> SEQUENCE: 16

Ser Ser Asn Ile Gly Ser Asn Thr
1               5

<210> SEQ ID NO 17
<211> LENGTH: 11
<212> TYPE: PRT
<213> ORGANISM: Homo sapiens

<400> SEQUENCE: 17

Ala Ser Trp Asp Asp Ser Leu Asn Gly Val Val
1               5                   10

<210> SEQ ID NO 18
<211> LENGTH: 6
<212> TYPE: PRT
<213> ORGANISM: Homo sapiens

<400> SEQUENCE: 18

Gln Ser Val Ser Arg Tyr
1               5

<210> SEQ ID NO 19
<211> LENGTH: 9
<212> TYPE: PRT
<213> ORGANISM: Homo sapiens

```
<400> SEQUENCE: 19

Gln Gln Thr Tyr Ser Thr Pro Trp Thr
1               5

<210> SEQ ID NO 20
<211> LENGTH: 9
<212> TYPE: PRT
<213> ORGANISM: Homo sapiens

<400> SEQUENCE: 20

Asn Ser Asn Ile Gly Ala Gly Tyr His
1               5

<210> SEQ ID NO 21
<211> LENGTH: 11
<212> TYPE: PRT
<213> ORGANISM: Homo sapiens

<400> SEQUENCE: 21

Gln Ser Tyr Asp Arg Ser Arg Gly Gly Trp Phe
1               5                   10

<210> SEQ ID NO 22
<211> LENGTH: 6
<212> TYPE: PRT
<213> ORGANISM: Homo sapiens

<400> SEQUENCE: 22

Asn Ile Ala Arg Lys Ser
1               5

<210> SEQ ID NO 23
<211> LENGTH: 9
<212> TYPE: PRT
<213> ORGANISM: Homo sapiens

<400> SEQUENCE: 23

Gln Val Trp Asp Asn Ser Asp Tyr Val
1               5

<210> SEQ ID NO 24
<211> LENGTH: 6
<212> TYPE: PRT
<213> ORGANISM: Homo sapiens

<400> SEQUENCE: 24

Gln Asn Ile Asn Ser Arg
1               5

<210> SEQ ID NO 25
<211> LENGTH: 9
<212> TYPE: PRT
<213> ORGANISM: Homo sapiens

<400> SEQUENCE: 25

Gln Gln Phe Asp Lys Tyr Ser Ile Thr
1               5

<210> SEQ ID NO 26
<211> LENGTH: 30
<212> TYPE: DNA
<213> ORGANISM: Homo sapiens
```

```
<400> SEQUENCE: 26
ggtggctccg tcagcagagg tagtcactac                              30

<210> SEQ ID NO 27
<211> LENGTH: 21
<212> TYPE: DNA
<213> ORGANISM: Homo sapiens

<400> SEQUENCE: 27
atccacaccg atgggagcac c                                       21

<210> SEQ ID NO 28
<211> LENGTH: 30
<212> TYPE: DNA
<213> ORGANISM: Homo sapiens

<400> SEQUENCE: 28
gcgagagagc ccgggggcgc cctgaatttc                              30

<210> SEQ ID NO 29
<211> LENGTH: 24
<212> TYPE: DNA
<213> ORGANISM: Homo sapiens

<400> SEQUENCE: 29
ggatacacct tcaccggcta ctat                                    24

<210> SEQ ID NO 30
<211> LENGTH: 24
<212> TYPE: DNA
<213> ORGANISM: Homo sapiens

<400> SEQUENCE: 30 atcaaccta acagtggtgg caca                                     24

<210> SEQ ID NO 31
<211> LENGTH: 57
<212> TYPE: DNA
<213> ORGANISM: Homo sapiens

<400> SEQUENCE: 31
gcgagtggga aaacgtatta cgatttttgg agtggtggga gacgcggtat ggacgtc    57

<210> SEQ ID NO 32
<211> LENGTH: 24
<212> TYPE: DNA
<213> ORGANISM: Homo sapiens

<400> SEQUENCE: 32
ggaggcacct tcagcagcta tgct                                    24

<210> SEQ ID NO 33
<211> LENGTH: 24
<212> TYPE: DNA
<213> ORGANISM: Homo sapiens

<400> SEQUENCE: 33
atcatcccta tctttggtac agca                                    24

<210> SEQ ID NO 34
<211> LENGTH: 45
<212> TYPE: DNA
<213> ORGANISM: Homo sapiens
```

<400> SEQUENCE: 34
gcgagaagcc aggtaccatc ctcctactac tacggtatgg acgtc            45

<210> SEQ ID NO 35
<211> LENGTH: 24
<212> TYPE: DNA
<213> ORGANISM: Homo sapiens

<400> SEQUENCE: 35
ggattcacct tcagtagcta tgct                                   24

<210> SEQ ID NO 36
<211> LENGTH: 24
<212> TYPE: DNA
<213> ORGANISM: Homo sapiens

<400> SEQUENCE: 36
atatcatatg atggaagcaa taaa                                   24

<210> SEQ ID NO 37
<211> LENGTH: 36
<212> TYPE: DNA
<213> ORGANISM: Homo sapiens

<400> SEQUENCE: 37
gcgagaggtc gtgaatacta ctactacatg gacgtc                      36

<210> SEQ ID NO 38
<211> LENGTH: 24
<212> TYPE: DNA
<213> ORGANISM: Homo sapiens

<400> SEQUENCE: 38
ggatacacct tcaccagcta ctat                                   24

<210> SEQ ID NO 39
<211> LENGTH: 24
<212> TYPE: DNA
<213> ORGANISM: Homo sapiens

<400> SEQUENCE: 39 atcaaccta gtggtggtag caca                                    24

<210> SEQ ID NO 40
<211> LENGTH: 39
<212> TYPE: DNA
<213> ORGANISM: Homo sapiens

<400> SEQUENCE: 40
gcgagaggat tcggctacgg tggtaaggcc cttgactac                   39

<210> SEQ ID NO 41
<211> LENGTH: 24
<212> TYPE: DNA
<213> ORGANISM: Homo sapiens

<400> SEQUENCE: 41
agctccaaca tcggaagtaa tact                                   24

<210> SEQ ID NO 42
<211> LENGTH: 33
<212> TYPE: DNA
<213> ORGANISM: Homo sapiens

```
<400> SEQUENCE: 42
gcatcatggg atgacagcct gaatggtgtg gta                           33

<210> SEQ ID NO 43
<211> LENGTH: 18
<212> TYPE: DNA
<213> ORGANISM: Homo sapiens

<400> SEQUENCE: 43
cagagcgtta gcaggtat                                           18

<210> SEQ ID NO 44
<211> LENGTH: 27
<212> TYPE: DNA
<213> ORGANISM: Homo sapiens

<400> SEQUENCE: 44
caacagactt acagtacccc gtggacg                                 27

<210> SEQ ID NO 45
<211> LENGTH: 27
<212> TYPE: DNA
<213> ORGANISM: Homo sapiens

<400> SEQUENCE: 45
aactccaaca tcggggcagg ttatcat                                 27

<210> SEQ ID NO 46
<211> LENGTH: 33
<212> TYPE: DNA
<213> ORGANISM: Homo sapiens

<400> SEQUENCE: 46
cagtcctatg acagaagccg gggtggttgg ttt                          33

<210> SEQ ID NO 47
<211> LENGTH: 18
<212> TYPE: DNA
<213> ORGANISM: Homo sapiens

<400> SEQUENCE: 47
aacattgcaa gaaaaagt                                           18

<210> SEQ ID NO 48
<211> LENGTH: 27
<212> TYPE: DNA
<213> ORGANISM: Homo sapiens

<400> SEQUENCE: 48
caggtgtggg ataatagtga ttatgtc                                 27

<210> SEQ ID NO 49
<211> LENGTH: 18
<212> TYPE: DNA
<213> ORGANISM: Homo sapiens

<400> SEQUENCE: 49
cagaatatta atagtagg                                           18

<210> SEQ ID NO 50
<211> LENGTH: 27
<212> TYPE: DNA
<213> ORGANISM: Homo sapiens
```

<400> SEQUENCE: 50
caacagtttg ataaatattc gatcact                                     27

<210> SEQ ID NO 51
<211> LENGTH: 354
<212> TYPE: DNA
<213> ORGANISM: Homo sapiens

<400> SEQUENCE: 51
caggtacagc tgcagcagtt gggcccagga ctggtgaagc cttcggagac cctgtccctc   60
acctgcaatg tctctggtgg ctccgtcagc agaggtagtc actactggac ctggatccgg  120
cagcccccag gaaagggact ggagtggatt gggtatatcc acaccgatgg gagcaccaac  180
ttcaatccct ccctcaagag tcgagtcacc atgtcactag acaggtccag gaaccagttc  240
tccctgacgc tgagctctgt gaccgctacg gacacggccg tttattattg tgcgagagag  300
cccgggggcg ccctgaattt ctggggccag ggaaccctgg tcaccgtctc ctca        354

<210> SEQ ID NO 52
<211> LENGTH: 330
<212> TYPE: DNA
<213> ORGANISM: Homo sapiens

<400> SEQUENCE: 52
aattttatgc tgactcagcc accctcaacg tctgggaccc ccgggcagag ggtcaccatc   60
tcttgttctg gaagcagctc aacatcgga agtaatactg taaactggta ccagcagctc  120
ccaggaacgg cccccaaact cctcatctat agtaataatc agcggccctc aggggtccct  180
gaccgattct ctggctccaa gtctggcacc tcagcctccc tggccatcag tgggctccag  240
tctgaggatg aggctgatta ttattgtgca tcatgggatg acagcctgaa tggtgtggta  300
ttcggcggag ggaccacggt gaccgtcctg                                   330

<210> SEQ ID NO 53
<211> LENGTH: 378
<212> TYPE: DNA
<213> ORGANISM: Homo sapiens

<400> SEQUENCE: 53
caggtgcagc tggtgcagtc tggggctgag gtgaagaagc ctggggcctc agtgaaggtc   60
tcctgcaagg cttctggata caccttcacc ggctactata tgcactgggt gcgacaggcc  120
cctggacaag gcttgagtg gatgggacgg atcaacccta acagtggtgg cacaaactat  180
gcacagaagt ttcagggcag ggtcaccatg accagggaca cgtccatcag cacagcctac  240
atggagctga gcaggctgag atctgacgac acggccgtgt attactgtgc gagtgggaaa  300
acgtattacg attttggag tggtgggaga cgcggtatgg acgtctgggg ccaagggaca  360
atggtcaccg tctcttca                                               378

<210> SEQ ID NO 54
<211> LENGTH: 321
<212> TYPE: DNA
<213> ORGANISM: Homo sapiens

<400> SEQUENCE: 54
gacatccagt tgacccagtc tccatcctcc ctgtctgcat ctgtaggaga cagagtcacc   60
atcacttgcc gggcaggtca gagcgttagc aggtatttaa attggtttca gcagaaacca  120
gggaaagccc ctaagctcct catctatact tcatccaatt tgcaaagtgg ggtcccatca  180
aggttcagtg ccagtggatc tgggacagat ttcactctca ccatcagcag tctgcaacct    240
gaggattttg ctacctacta ctgtcaacag acttacagta ccccgtggac gttcggccaa    300
gggaccaagc tggagatcaa a    321

<210> SEQ ID NO 55
<211> LENGTH: 366
<212> TYPE: DNA
<213> ORGANISM: Homo sapiens

<400> SEQUENCE: 55
caggtgcagc tggtgcagtc tggggctgag gtgaagaagc ctgggtcctc ggtgaaggtc     60
tcctgcaagg cttctggagg caccttcagc agctatgcta tcagctgggt gcgacaggcc    120
cctggacaag gcttgagtg gatgggaggg atcatcccta tctttggtac agcaaactac    180
gcacagaagt tccagggcag agtcacgatt accgcggacg aatccacgag cacagcctac    240
atggagctga gcagcctgag atctgaggac acggccgtgt attactgtgc gagaagccag    300
gtaccatcct cctactacta cggtatggac gtctggggcc aagggacaat ggtcaccgtc    360
tcctca    366

<210> SEQ ID NO 56
<211> LENGTH: 333
<212> TYPE: DNA
<213> ORGANISM: Homo sapiens

<400> SEQUENCE: 56
cagtctgtgc tgactcagcc gccctcagtg tctggggccc cagggcagag ggtcaccatc     60
tcctgcactg ggggcaactc caacatcggg gcaggttatc atgtacattg gtaccagcaa    120
cttccaggag cagcccccaa actcctcatc tatggtgaca ctaatcggcc ctcaggggtc    180
cctgaccgat tctctggctc tcagtctggc acctcagcct ccctggccat cactgggctc    240
caggctgacg atgaggctga ttattactgc cagtcctatg acagaagccg gggtggttgg    300
tttttcggcg gagggaccca gctgaccgtc cta    333

<210> SEQ ID NO 57
<211> LENGTH: 357
<212> TYPE: DNA
<213> ORGANISM: Homo sapiens

<400> SEQUENCE: 57
caggtgaagc tggtggagtg gtcgctgagc gtggtccagc ctggggaggtc cctgagactc     60 tcctgcgcag cctctggatt caccttcagt agctatgcta tgcactgggt ccgccaggct    120
ccaggcaagg gctggagtg gtggcagtt atatcatatg atggaagcaa taaatactac    180
gcagactccg tgaagggccg attcaccatc tccagagaca attccaagaa cacgctgtat    240
ctgcaaatga acagcctgag agctgaggac acggctgtgt attactgtgc gagaggtcgt    300
gaatactact actacatgga cgtctggggc aaagggacca cggtcagcgt ctcctca    357

<210> SEQ ID NO 58
<211> LENGTH: 318
<212> TYPE: DNA
<213> ORGANISM: Homo sapiens

<400> SEQUENCE: 58
cagtctgtgc tgactcagcc accctcagtg tcagtggccc caggaaagac ggccaggatt     60
acatgtgggg gatacaacat tgcaagaaaa agtgtgcact ggtaccagca gaagccaggc    120

```
caggcccctg tgttggtcat gtataatgat aacgaccggc cctcagggat ccctgagcga        180
ttctctggct ccaactctgg gaacacggcc accctgacca tcagcagggt cgaagccggg        240
gatgaggccg actattactg tcaggtgtgg gataatagtg attatgtctt cggaactggg        300
accaaggtca ccgtccta                                                      318

<210> SEQ ID NO 59
<211> LENGTH: 360
<212> TYPE: DNA
<213> ORGANISM: Homo sapiens

<400> SEQUENCE: 59
caggtgcagt tgatgcagtc tggggctgag gtgaagaagc ctggggcctc agtgaaggtt         60
tcctgcaagg catctggata caccttcacc agctactata tgcactgggt gcgacaggcc        120
cctggacaag gcttgagtg gatgggaata atcaaccctá gtggtggtag cacaagctac        180
gcacagaagt tccagggcag agtcaccatg accagggaca cgtccacgag cacagtctac        240
atggagctga gcagcctgag atctgaggac acggccgtgt attactgtgc gagaggattc        300
ggctacggtg gtaaggccct tgactactgg ggccagggaa ccacggtcac cgtctcttca        360

<210> SEQ ID NO 60
<211> LENGTH: 321
<212> TYPE: DNA
<213> ORGANISM: Homo sapiens

<400> SEQUENCE: 60
gacatccaga tgacccagtc tcctcccacc ctgtctgcat ctgtagggga cagagtcacc         60
atcacttgcc gggccagtca gaatattaat agtaggttgg cctggtatca gcagaaacca        120
gggagagccc ctaaactcct gatctataag gcgtctactt tagagagtgg ggtcccatcg        180
aggttcagcg gcagtggatc tgggacagaa ttcactctca ccatcagcag cctgcagcca        240
gatgactttg caacttatta ctgccaacag tttgataaat attcgatcac tttcggcgga        300
gggaccaaga tggagatcaa a                                                  321

<210> SEQ ID NO 61
<211> LENGTH: 118
<212> TYPE: PRT
<213> ORGANISM: Homo sapiens

<400> SEQUENCE: 61

Gln Val Gln Leu Gln Gln Leu Gly Pro Gly Leu Val Lys Pro Ser Glu
1               5                   10                  15

Thr Leu Ser Leu Thr Cys Asn Val Ser Gly Ser Val Ser Arg Gly
            20                  25                  30

Ser His Tyr Trp Thr Trp Ile Arg Gln Pro Pro Gly Lys Gly Leu Glu
        35                  40                  45

Trp Ile Gly Tyr Ile His Thr Asp Gly Ser Thr Asn Phe Asn Pro Ser
    50                  55                  60

Leu Lys Ser Arg Val Thr Met Ser Leu Asp Arg Ser Arg Asn Gln Phe
65                  70                  75                  80

Ser Leu Thr Leu Ser Ser Val Thr Ala Thr Asp Thr Ala Val Tyr Tyr
                85                  90                  95

Cys Ala Arg Glu Pro Gly Gly Ala Leu Asn Phe Trp Gly Gln Gly Thr
            100                 105                 110

Leu Val Thr Val Ser Ser
        115
```

<210> SEQ ID NO 62
<211> LENGTH: 110
<212> TYPE: PRT
<213> ORGANISM: Homo sapiens

<400> SEQUENCE: 62

Asp Phe Met Leu Thr Gln Pro Pro Ser Thr Ser Gly Thr Pro Gly Gln
1               5                   10                  15

Arg Val Thr Ile Ser Cys Ser Gly Ser Ser Asn Ile Gly Ser Asn
            20                  25                  30

Thr Val Asn Trp Tyr Gln Gln Leu Pro Gly Thr Ala Pro Lys Leu Leu
            35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Gln
65                  70                  75                  80

Ser Glu Asp Glu Ala Asp Tyr Tyr Cys Ala Ser Trp Asp Asp Ser Leu
                85                  90                  95

Asn Gly Val Val Phe Gly Gly Gly Thr Val Thr Val Leu
            100                 105                 110

<210> SEQ ID NO 63
<211> LENGTH: 126
<212> TYPE: PRT
<213> ORGANISM: Homo sapiens

<400> SEQUENCE: 63

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gly Tyr
            20                  25                  30

Tyr Met His Trp Val Arg Gln Ala Pro Gly Gln Gly Leu Glu Trp Met
            35                  40                  45

Gly Arg Ile Asn Pro Asn Ser Gly Gly Thr Asn Tyr Ala Gln Lys Phe
    50                  55                  60

Gln Gly Arg Val Thr Met Thr Arg Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Ser Gly Lys Thr Tyr Tyr Asp Phe Trp Ser Gly Arg Arg Gly
            100                 105                 110

Met Asp Val Trp Gly Gln Gly Thr Met Val Thr Val Ser Ser
            115                 120                 125

<210> SEQ ID NO 64
<211> LENGTH: 107
<212> TYPE: PRT
<213> ORGANISM: Homo sapiens

<400> SEQUENCE: 64

Asp Ile Gln Leu Thr Gln Ser Pro Ser Ser Leu Ser Ala Ser Val Gly
1               5                   10                  15

Asp Arg Val Thr Ile Thr Cys Arg Ala Gly Gln Ser Val Ser Arg Tyr
            20                  25                  30

Leu Asn Trp Phe Gln Gln Lys Pro Gly Lys Ala Pro Lys Leu Leu Ile
            35                  40                  45

Tyr Thr Ser Ser Asn Leu Gln Ser Gly Val Pro Ser Arg Phe Ser Ala
    50                  55                  60

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Thr Tyr Ser Thr Pro Trp
             85                  90                  95

Thr Phe Gly Gln Gly Thr Lys Leu Glu Ile Lys
            100                 105
```

<210> SEQ ID NO 65
<211> LENGTH: 122
<212> TYPE: PRT
<213> ORGANISM: Homo sapiens

<400> SEQUENCE: 65

```
Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
             20                  25                  30

Ala Ile Ser Trp Val Arg Gln Ala Pro Gly Gln Gly Leu Glu Trp Met
         35                  40                  45

Gly Gly Ile Ile Pro Ile Phe Gly Thr Ala Asn Tyr Ala Gln Lys Phe
     50                  55                  60

Gln Gly Arg Val Thr Ile Thr Ala Asp Glu Ser Thr Ser Thr Ala Tyr
 65                  70                  75                  80

Met Glu Leu Ser Ser Leu Arg Ser Glu Asp Thr Ala Val Tyr Tyr Cys
             85                  90                  95

Ala Arg Ser Gln Val Pro Ser Ser Tyr Tyr Tyr Gly Met Asp Val Trp
            100                 105                 110

Gly Gln Gly Thr Met Val Thr Val Ser Ser
        115                 120
```

<210> SEQ ID NO 66
<211> LENGTH: 111
<212> TYPE: PRT
<213> ORGANISM: Homo sapiens

<400> SEQUENCE: 66

```
Gln Ser Val Leu Thr Gln Pro Pro Ser Val Ser Gly Ala Pro Gly Gln
 1               5                  10                  15

Arg Val Thr Ile Ser Cys Thr Gly Asn Ser Asn Ile Gly Ala Gly
             20                  25                  30

Tyr His Val His Trp Tyr Gln Gln Leu Pro Gly Ala Ala Pro Lys Leu
         35                  40                  45

Leu Ile Tyr Gly Asp Thr Asn Arg Pro Ser Gly Val Pro Asp Arg Phe
     50                  55                  60

Ser Gly Ser Gln Ser Gly Thr Ser Ala Ser Leu Ala Ile Thr Gly Leu
 65                  70                  75                  80

Gln Ala Asp Asp Glu Ala Asp Tyr Tyr Cys Gln Ser Tyr Asp Arg Ser
             85                  90                  95

Arg Gly Gly Trp Phe Phe Gly Gly Thr Gln Leu Thr Val Leu
            100                 105                 110
```

<210> SEQ ID NO 67
<211> LENGTH: 119
<212> TYPE: PRT
<213> ORGANISM: Homo sapiens

```
<400> SEQUENCE: 67

Gln Val Lys Leu Val Glu Trp Ser Leu Ser Val Val Gln Pro Gly Arg
1               5                   10                  15

Ser Leu Arg Leu Ser Cys Ala Ala Ser Gly Phe Thr Phe Ser Ser Tyr
            20                  25                  30

Ala Met His Trp Val Arg Gln Ala Pro Gly Lys Gly Leu Glu Trp Val
        35                  40                  45

Ala Val Ile Ser Tyr Asp Gly Ser Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Arg Glu Tyr Tyr Tyr Met Asp Val Trp Gly Lys Gly
            100                 105                 110

Thr Thr Val Ser Val Ser Ser
        115

<210> SEQ ID NO 68
<211> LENGTH: 106
<212> TYPE: PRT
<213> ORGANISM: Homo sapiens

<400> SEQUENCE: 68

Gln Ser Val Leu Thr Gln Pro Pro Ser Val Ser Val Ala Pro Gly Lys
1               5                   10                  15

Thr Ala Arg Ile Thr Cys Gly Gly Tyr Asn Ile Ala Arg Lys Ser Val
            20                  25                  30

His Trp Tyr Gln Gln Lys Pro Gly Gln Ala Pro Val Leu Val Met Tyr
        35                  40                  45

Asn Asp Asn Asp Arg Pro Ser Gly Ile Pro Glu Arg Phe Ser Gly Ser
    50                  55                  60

Asn Ser Gly Asn Thr Ala Thr Leu Thr Ile Ser Arg Val Glu Ala Gly
65                  70                  75                  80

Asp Glu Ala Asp Tyr Tyr Cys Gln Val Trp Asp Asn Ser Asp Tyr Val
                85                  90                  95

Phe Gly Thr Gly Thr Lys Val Thr Val Leu
            100                 105

<210> SEQ ID NO 69
<211> LENGTH: 120
<212> TYPE: PRT
<213> ORGANISM: Homo sapiens

<400> SEQUENCE: 69

Gln Val Gln Leu Met Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Met His Trp Val Arg Gln Ala Pro Gly Gln Gly Leu Glu Trp Met
        35                  40                  45

Gly Ile Ile Asn Pro Ser Gly Gly Ser Thr Tyr Ala Gln Lys Phe
    50                  55                  60

Gln Gly Arg Val Thr Met Thr Arg Asp Thr Ser Thr Ser Thr Val Tyr
65                  70                  75                  80
```

```
Met Glu Leu Ser Ser Leu Arg Ser Glu Asp Thr Ala Val Tyr Tyr Cys
                85                  90                  95

Ala Arg Gly Phe Gly Tyr Gly Lys Ala Leu Asp Tyr Trp Gly Gln
            100                 105                 110

Gly Thr Thr Val Thr Val Ser Ser
        115             120

<210> SEQ ID NO 70
<211> LENGTH: 107
<212> TYPE: PRT
<213> ORGANISM: Homo sapiens

<400> SEQUENCE: 70

Asp Ile Gln Met Thr Gln Ser Pro Pro Thr Leu Ser Ala Ser Val Gly
1               5                   10                  15

Asp Arg Val Thr Ile Thr Cys Arg Ala Ser Gln Asn Ile Asn Ser Arg
            20                  25                  30

Leu Ala Trp Tyr Gln Gln Lys Pro Gly Arg Ala Pro Lys Leu Leu Ile
            35                  40                  45

Tyr Lys Ala Ser Thr Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Phe Asp Lys Tyr Ser Ile
                85                  90                  95

Thr Phe Gly Gly Gly Thr Lys Met Glu Ile Lys
                100                 105
```

LEPTIN ANTIBODIES

REFERENCE TO A SEQUENCE LISTING

A Sequence Listing in text format is incorporated by reference into the specification. The name of the text file containing the Sequence Listing is 17124481.txt. The text file is 23731 bytes and was created and submitted electronically via EFS-Web on Mar. 12, 2021.

INTRODUCTION

Leptin is a hormone produced by adipocytes and is elevated in obesity. The congenital lack of leptin results in obesity and the metabolism field widely accepts the concept. Upon cloning of the leptin gene, the original hope was that leptin would act as a break for further food intake and a trigger to increase energy expenditure. The hope was that the injection of recombinant leptin would act as an effective weight loss mechanism. However, these hopes were quickly disappointed, since obese individuals have high leptin levels, but the individual is leptin resistant. Not even the injection of very high leptin levels can overcome this resistance.

We generated a battery of monoclonal antibodies against human and mouse leptin. These antibodies showed strong binding affinities to human leptin and significant neutralizing activity in vivo. More importantly, treatment of high-fat diet (HFD)-fed mice with neutralizing antibodies reduces body-weight gain and confirmed findings in mice with genetic knock-down of leptin. Our antibodies provide effective for treatment of obesity with high level of leptin but resistant to the conventional leptin treatment.

SUMMARY OF THE INVENTION

In an aspect the invention provides an antibody antigen binding domain which specifically binds human leptin, and comprises $V_H$ or $V_L$ CDR1, CDR2 and CDR3 sequences of an hLept antibody:

|  | CDR1 | CDR2 | CDR3 |
|---|---|---|---|
| $V_H$ | | | |
| hLept-1$V_H$ | GGSVSRGSHY (SEQ ID NO: 1) | IHTDGST (SEQ ID NO: 2) | AREPGGALNF (SEQ ID NO: 3) |
| hLept-2$V_H$ | GYTFTGYY (SEQ ID NO: 4) | INPNSGGT (SEQ ID NO: 5) | ASGKTYYDFWSGGRRGMDV (SEQ ID NO: 6) |
| hLept-3$V_H$ | GGTFSSYA (SEQ ID NO: 7) | IIPIFGTA (SEQ ID NO: 8) | ARSQVPSSYYYGMDV (SEQ ID NO: 9) |
| hLept-5$V_H$ | GFTFSSYA (SEQ ID NO: 10) | ISYDGSNK (SEQ ID NO: 11) | ARGREYYYYMDV (SEQ ID NO: 12) |
| hLept-6$V_H$ | GYTFTSYY (SEQ ID NO: 13) | INPSGGST (SEQ ID NO: 14) | ARGFGYGGKALDY (SEQ ID NO: 15) |
| $V_L$ | | | |
| hLept-1$V_L$ | SSNIGSNT (SEQ ID NO: 16) | SNN | ASWDDSLNGVV (SEQ ID NO: 17) |
| hLept-2$V_L$ | QSVSRY (SEQ ID NO: 18) | TSS | QQTYSTPWT (SEQ ID NO: 19) |
| hLept-3$V_L$ | NSNIGAGYH (SEQ ID NO: 20) | GDT | QSYDRSRGGWF (SEQ ID NO: 21) |
| hLept-5$V_L$ | NIARKS (SEQ ID NO: 22) | NDN | QVWDNSDYV (SEQ ID NO: 23) |
| hLept-6$V_L$ | QNINSR (SEQ ID NO: 24) | KAS | QQFDKYSIT (SEQ ID NO: 25) |

The $V_H$ and $V_L$ CDR1, CDR2 and CDR3 sequences of the hLept antibodies can be combined in alternative combinations which bind human leptin, i.e. the CDRs of hLept-1$V_H$ can be paired with the CDRs of hLept-1-$V_L$, hLept-2$V_L$, hLept-3$V_L$, hLept-5$V_L$ or hLept-6$V_L$.

In embodiments the antigen binding domain comprises:
$V_H$ and $V_L$ CDR1, CDR2 and CDR3 sequences of the hLept antibody;
$V_H$ or $V_L$ sequences of the hLept antibody; and/or
$V_H$ and $V_L$ sequences of the hLept antibody.

In embodiments the antigen binding domain is part of a monoclonal IgG antibody and/or a humanized antibody.

In other aspects the invention provides an expression vector encoding the antibody antigen binding domain or a cultured cell expressing the antibody antigen binding domain.

In another aspect the invention provides a method of using the antibody antigen binding domain to treat obesity or diabetes, comprising the step of administering the domain to a person in need thereof.

The invention includes all combinations of the recited particular embodiments.

BRIEF DESCRIPTION OF THE DRAWINGS

FIG. 1A. Antibody therapy reduces body weight.
FIG. 1B. Antibody therapy reduces food intake.
FIG. 1C. Antibody therapy increases leptin transcription in brown and epididymal adipose tissue.
FIG. 1D. Antibody therapy improves glucose homeostasis.
FIG. 1E. Antibody therapy reduces high fat diet effects on brown adipose tissue.

DESCRIPTION OF PARTICULAR EMBODIMENTS OF THE INVENTION

Unless the context indicates otherwise, the term "antibody" is used in the broadest sense and specifically covers antibodies (including full length monoclonal antibodies) and antibody fragments. An antibody molecule is usually monospecific, but may also be described as idiospecific, heterospecific, or polyspecific. Antibody molecules bind by means of specific binding sites to specific antigenic determinants or epitopes on antigens. "Antibody fragments" comprise a portion of a full length antibody, generally the antigen binding or variable region thereof. Examples of antibody fragments include Fab, Fab', F(ab').sub.2, and Fv fragments; diabodies; linear antibodies; single-chain antibody molecules; and multispecific antibodies formed from antibody fragments.

Natural and engineered antibody structures are well known in the art, e.g. Strohl et al., *Therapeutic antibody engineering: Current and future advances driving the strongest growth area in the pharmaceutical industry*, Woodhead Publishing Series in Biomedicine No. 11, October 2012; Holliger et al. Nature Biotechnol 23, 1126-1136 (2005); Chames et al. Br J Pharmacol. 2009 May; 157(2): 220-233.

Monoclonal antibodies (MAbs) may be obtained by methods known to those skilled in the art. See, for example Kohler et al (1975); U.S. Pat. No. 4,376,110; Ausubel et al (1987-1999); Harlow et al (1988); and Colligan et al (1993). The mAbs of the invention may be of any immunoglobulin class including IgG, IgM, IgE, IgA, and any subclass thereof. A hybridoma producing a mAb may be cultivated in vitro or in vivo. High titers of mAbs can be obtained in in vivo production where cells from the individual hybridomas are injected intraperitoneally into mice, such as pristine-primed Balb/c mice to produce ascites fluid containing high concentrations of the desired mAbs. MAbs of isotype IgM or IgG may be purified from such ascites fluids, or from culture supernatants, using column chromatography methods well known to those of skill in the art.

An "isolated polynucleotide" refers to a polynucleotide segment or fragment which has been separated from sequences which flank it in a naturally occurring state, e.g., a DNA fragment which has been removed from the sequences which are normally adjacent to the fragment, e.g., the sequences adjacent to the fragment in a genome in which it naturally occurs. The term therefore includes, for example, a recombinant DNA which is incorporated into a vector, into an autonomously replicating plasmid or virus, or into the genomic DNA of a prokaryote or eukaryote, or which exists as a separate molecule (e.g., as a cDNA or a genomic or cDNA fragment produced by PCR or restriction enzyme digestion) independent of other sequences. It also includes a recombinant DNA, which is part of a hybrid gene encoding additional polypeptide sequence.

A "construct" means any recombinant polynucleotide molecule such as a plasmid, cosmid, virus, autonomously replicating polynucleotide molecule, phage, or linear or circular single-stranded or double-stranded DNA or RNA polynucleotide molecule, derived from any source, capable of genomic integration or autonomous replication, comprising a polynucleotide molecule where one or more polynucleotide molecule has been linked in a functionally operative manner, i.e. operably linked. A recombinant construct will typically comprise the polynucleotides of the invention operably linked to transcriptional initiation regulatory sequences that will direct the transcription of the polynucleotide in the intended host cell. Both heterologous and non-heterologous (i.e., endogenous) promoters can be employed to direct expression of the nucleic acids of the invention.

A "vector" refers any recombinant polynucleotide construct that may be used for the purpose of transformation, i.e. the introduction of heterologous DNA into a host cell. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors".

An "expression vector" as used herein refers to a nucleic acid molecule capable of replication and expressing a gene of interest when transformed, transfected or transduced into a host cell. The expression vectors comprise one or more phenotypic selectable markers and an origin of replication to ensure maintenance of the vector and to, if desired, provide amplification within the host. The expression vector further comprises a promoter to drive the expression of the polypeptide within the cells. Suitable expression vectors may be plasmids derived, for example, from pBR322 or various pUC plasmids, which are commercially available. Other expression vectors may be derived from bacteriophage, phagemid, or cosmid expression vectors.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein, including citations therein, are hereby incorporated by reference in their entirety for all purposes.

EXAMPLES

Panning and Selection of Anti-Leptin Monoclonal Antibodies Using In-House Prepared scFv Phage Display Human Antibody Library Leptin protein (NM-000230, Entrez 3952: Sino Biologics) was used to panning the phage display scFv library (diversity of $1\times10^{11}$). Binders were selected by phage ELISA by coating LEPTIN protein on 96-well plates (maxsorb plates, Nunc) and were detected with an anti-M13 phage antibody conjugated with horseradish peroxidase (HRP) and TMB substrate (cell signaling). DNA sequences contained in phage-mid vector is isolated using a plasmid preparation kit and sequenced (Genewiz). Complete heavy chain variable region and light chain variable sequences were amplified and expressed into full IgG using an expression vector system in HEK293 cells.

Selected LEPTIN binding hits were expressed as human IgGs using a mammalian expression vector system in human embryonic kidney (HEK293) cells (Invitrogen). Antibodies were purified using a column with protein A resin by a fast protein liquid chromatography (FPLC) separation unit. Purified LEPTIN binding antibodies were characterized for their biological properties.

Binding Affinity of Anti-Leptin Monoclonal Antibodies

Binding of LEPTIN by monoclonal antibodies was first screened by ELISA using supernatants collected from the B cell cultures. Human or mouse LEPTIN protein (Sino Biologicals) was coated on a 96-well high binding plate over night at 4° C. in PBS. B cell culture supernatants (5 µl medium and 95 µl of PBS) were added at for binding to LEPTIN antigen coated on the plate. Bound antibody was detected using a secondary antibody against rabbit IgG conjugated with HRP and TMB substrate.

Binding to human leptin in ELISA (1:20 diluted culture supernatants; signals: absorbance at 450 nM):

| hLept-1/ | hLept-2/ | hLept-3/ | hLept-5/ | hLept-6/ |
|---|---|---|---|---|
| 0.071 | 2.5739 | 0.1902 | 0.7385 | 0.663 |

ELISA titration was used to determine the binding affinity of a panel of monoclonal antibodies to LEPTIN antigen. Binding constants ($K_D$ and/or EC 50) of a panel of monoclonal antibodies were estimated using the 4 parameter curve fitting with Prism GraphPad program. For Biacore analysis, all experiments were performed at 25° C. at a flow rate of 45 µl/min. An anti-human IgG Fc antibody (from ThermoFisher, at 50 µg/ml each in acetate buffer, pH 5.0) was immobilized onto a carboxymethyl dextran sensorchip (CMS) using amine coupling procedures based on instruction from the manufacturer. Purified rabbit/human chimeric antibody to be tested was diluted at a concentration of 5 µg/ml in 0.5% P20, HBS-EP buffer and injected on FC2 to reach 500 to 1000 RU. FC1 was used as the reference cell. Specific signals correspond to the difference of signals obtained on FC2 versus FC1. The analyte (recombinant human LEPTIN, apparent molecular weight 16 kDa on SDS-PAGE gel) was injected during 90 sec at series of concentration dilutions (100, 50, 25, 12.5, 6.25, and 3.13, 1.56 nM) in 0.5% P20, HBS-EP buffer. These concentrations were prepared from stock solution in 0.5% P20, HBS-EP. The dissociation phase of the analyte was monitored over a 30 minutes period. Running buffer was also injected under the same conditions as a double reference. After each running cycle, both flow cells were regenerated by injecting 20 to 45 µl of Glycine-HCl buffer pH 1.5. Binding $K_D$ on LEPTIN was calculated by $k_{off}/k_{on}$ kinetic rate for each LEPTIN monoclonal antibodies (Table 3).

Neutralizing Leptin Antibodies Confer Reduced Weight Gain.

We used a cohort of mice that had previously been exposed to 10 weeks of high fat diet exposure. We treated these mice twice a week either with PBS, low ("0.5 microgram/g BW), medium (5 microgram/g BW) or high (50 microgram/g BW) leptin antibody injections for up to 20 days; hLept-1, hLept-2, hLept-3, hLept-5 and hLept-6 antibody injections provide consistent dose dependent results. As seen in FIG. 1A, there is a dose-dependent effect of these injections in terms of impaired weight gain. While all animals initially lost some weight, control mice and lower doses of antibody had some effect, whereas with the highest dose of antibody, overall weight reduction persisted. There was a dose-dependent reduction in food intake (FIG. 1B), as well as a dose-dependent transcriptional increase for leptin in brown and epididymal adipose tissue, with more limited compensatory effects in subcutaneous adipose tissue (FIG. 1C). Antibody treatment leads to an effective 40% reduction of circulating leptin levels, sufficient to achieve a significant degree of leptin sensitization. Leptin-neutralization not only effectively reduces the weight, but with the weight reduction we also see the expected improvements in glucose homeostasis (FIG. 1D). Furthermore, high fat diet generally affects brown adipose tissue negatively and lead to an increased "whitening" of BAT, and this process is significantly prevented and/or reversed by our antibody treatment (FIG. 1E). Concomitantly, we also observed a reduction in hepatic steatosis.

TABLE 1

CDR* sequences of heavy chain variable sequences of leptin antibodies

| Name | CDR1 | CDR2 | CDR3 |
|---|---|---|---|
| hLept-1 | Ggtggctccgtcagc agaggtagtcactac (SEQ ID NO: 26) GGSVSRGSHY (SEQ ID NO: 1) | Atccacaccgatggg agcacc (SEQ ID NO: 27) IHTDGST (SEQ ID NO: 2) | Gcgagagagcccggg ggcgccctgaatttc (SEQ ID NO: 28) AREPGGALNF (SEQ ID NO: 3) |
| hLept-2 | Ggatacaccttcacc ggctactat (SEQ ID NO: 29) GYTFTGYY (SEQ ID NO: 4) | Atcaaccctaacagt ggtggcaca (SEQ ID NO: 30) INPNSGGT (SEQ ID NO: 5) | Gcgagtgggaaaacg tattacgattttttgg agtggtgggagacgc ggtatggacgtc (SEQ ID NO: 31) ASGKTYYDFWSGGRR GMDV (SEQ ID NO: 6) |
| hLept-3 | Ggaggcaccttcagc agctatgct (SEQ ID NO: 32) GGTFSSYA (SEQ ID NO: 7) | Atcatccctatcttt ggtacagca (SEQ ID NO: 33) IIPIFGTA (SEQ ID NO: 8) | Gcgagaagccaggta ccatcctcctactac tacggtatggacgtc (SEQ ID NO: 34) ARSQVPSSYYYGMDV (SEQ ID NO: 9) |

TABLE 1-continued

CDR* sequences of heavy chain variable sequences of leptin antibodies

| Name | CDR1 | CDR2 | CDR3 |
|---|---|---|---|
| hLept-5 | Ggattcaccttcagt agctatgct (SEQ ID NO: 35) GFTFSSYA (SEQ ID NO: 10) | Atatcatatgatgga agcaataaa (SEQ ID NO: 36) ISYDGSNK (SEQ ID NO: 11) | Gcgagaggtcgtgaa tactactactacatg gacgtc (SEQ ID NO: 37) ARGREYYYYMDV (SEQ ID NO: 12) |
| hLept-6 | Ggatacaccttcacc agctactat (SEQ ID NO: 38) GYTFTSYY (SEQ ID NO: 13) | Atcaaccctagtggt ggtagcaca (SEQ ID NO: 39) INPSGGST (SEQ ID NO: 14) | Gcgagaggattcggc tacggtggtaaggcc cttgactac (SEQ ID NO: 40) ARGFGYGGKALDY (SEQ ID NO: 15) |

*CDRs are defined based on online antibody sequence analytical tool (IMGT).

TABLE 2

List of CDR sequences for light chain of each antibodies

| Name | CDR1 | CDR2 | CDR3 |
|---|---|---|---|
| hLept-1 | Agctccaacatcgga agtaatact (SEQ ID NO: 41) SSNIGSNT (SEQ ID NO: 16) | agtaa taat SNN | Gcatcatgggatgac agcctgaatggtgtg gta (SEQ ID NO: 42) ASWDDSLNGVV (SEQ ID NO: 17) |
| hLept-2 | Cagagcgttagcagg tat (SEQ ID NO: 43) QSVSRY (SEQ ID NO: 18) | acttc atcc TSS | Caacagacttacagt accccgtggacg (SEQ ID NO: 44) QQTYSTPWT (SEQ ID NO: 19) |
| hLept-3 | Aactccaacatcggg gcaggttatcat (SEQ ID NO: 45) NSNIGAGYH (SEQ ID NO: 20) | ggtga cact GDT | Cagtcctatgacaga agccggggtggttgg ttt (SEQ ID NO: 46) QSYDRSRGGWF (SEQ ID NO: 21) |
| hLept-5 | Aacattgcaagaaaa agt (SEQ ID NO: 47) NIARKS (SEQ ID NO: 22) | aatga taac NDN | caggtgtgggataat agtgattatgtc (SEQ ID NO: 48) QVWDNSDYV (SEQ ID NO: 23) |
| hLept-6 | Cagaatattaatagt agg (SEQ ID NO: 49) QNINSR (SEQ ID NO: 24) | aaggc gtct KAS | Caacagtttgataaa tattcgatcact (SEQ ID NO: 50) QQFDKYSIT (SEQ ID NO: 25) |

TABLE 3

Binding affinities of anti-Leptin antibodies determined by ELISA

| Antibody name | EC50 |
|---|---|
| hLept-1 | 1-500 nM |
| hLept-2 | 1-500 nM |
| hLept-3 | 1-500 nM |
| hLept-5 | 1-500 nM |
| hLept-6 | 1-500 nM |

APPENDIX I

Variable DNA sequences of anti-leptin antibodies

>hLept1_HCv (SEQ ID NO: 51)
CAGGTACAGCTGCAGCAGTTGGGCCCAGGACTGGTGAAGCCTTCGGAGACCCTGTCCCTCACCT

GCAATGTCTCTGGTGGCTCCGTCAGCAGAGGTAGTCACTACTGGACCTGGATCCGGCAGCCCCC

AGGAAAGGGACTGGAGTGGATTGGGTATATCCACACCGATGGGAGCACCAACTTCAATCCCTCC

CTCAAGAGTCGAGTCACCATGTCACTAGACAGGTCCAGGAACCAGTTCTCCCTGACGCTGAGCT

CTGTGACCGCTACGGACACGGCCGTTTATTATTGTGCGAGAGAGCCCGGGGGCGCCCTGAATTT

CTGGGGCCAGGGAACCCTGGTCACCGTCTCCTCA

APPENDIX I-continued

Variable DNA sequences of anti-leptin antibodies

>hLept1_LCv
(SEQ ID NO: 52)
AATTTTATGCTGACTCAGCCACCCTCAACGTCTGGGACCCCCGGGCAGAGGGTCACCATCTCTT

GTTCTGGAAGCAGCTCCAACATCGGAAGTAATACTGTAAACTGGTACCAGCAGCTCCCAGGAAC

GGCCCCCAAACTCCTCATCTATAGTAATAATCAGCGGCCCTCAGGGGTCCCTGACCGATTCTCT

GGCTCCAAGTCTGGCACCTCAGCCTCCCTGGCCATCAGTGGGCTCCAGTCTGAGGATGAGGCTG

ATTATTATTGTGCATCATGGGATGACAGCCTGAATGGTGTGGTATTCGGCGGAGGGACCACGGT

GACCGTCCTG

>hLept2_HCv
(SEQ ID NO: 53)
CAGGTGCAGCTGGTGCAGTCTGGGGCTGAGGTGAAGAAGCCTGGGGCCTCAGTGAAGGTCTCCT

GCAAGGCTTCTGGATACACCTTCACCGGCTACTATATGCACTGGGTGCGACAGGCCCCTGGACA

AGGGCTTGAGTGGATGGGACGGATCAACCCTAACAGTGGTGGCACAAACTATGCACAGAAGTTT

CAGGGCAGGGTCACCATGACCAGGGACACGTCCATCAGCACAGCCTACATGGAGCTGAGCAGGC

TGAGATCTGACGACACGGCCGTGTATTACTGTGCGAGTGGGAAAACGTATTACGATTTTTGGAG

TGGTGGGAGACGCGGTATGGACGTCTGGGGCCAAGGGACAATGGTCACCGTCTCTTCA

>hLept2_LCv
(SEQ ID NO: 54)
GACATCCAGTTGACCCAGTCTCCATCCTCCCTGTCTGCATCTGTAGGAGACAGAGTCACCATCA

CTTGCCGGGCAGGTCAGAGCGTTAGCAGGTATTTAAATTGGTTTCAGCAGAAACCAGGGAAAGC

CCCTAAGCTCCTCATCTATACTTCATCCAATTTGCAAAGTGGGGTCCCATCAAGGTTCAGTGCC

AGTGGATCTGGGACAGATTTCACTCTCACCATCAGCAGTCTGCAACCTGAGGATTTTGCTACCT

ACTACTGTCAACAGACTTACAGTACCCCGTGGACGTTCGGCCAAGGGACCAAGCTGGAGATCAA

A

>hLept3_HCv
(SEQ ID NO: 55)
CAGGTGCAGCTGGTGCAGTCTGGGGCTGAGGTGAAGAAGCCTGGGTCCTCGGTGAAGGTCTCCT

GCAAGGCTTCTGGAGGCACCTTCAGCAGCTATGCTATCAGCTGGGTGCGACAGGCCCCTGGACA

AGGGCTTGAGTGGATGGGAGGGATCATCCCTATCTTTGGTACAGCAAACTACGCACAGAAGTTC

CAGGGCAGAGTCACGATTACCGCGGACGAATCCACGAGCACAGCCTACATGGAGCTGAGCAGCC

TGAGATCTGAGGACACGGCCGTGTATTACTGTGCGAGAAGCCAGGTACCATCCTCCTACTACTA

CGGTATGGACGTCTGGGGCCAAGGGACAATGGTCACCGTCTCCTCA

>hLept3_LCv
(SEQ ID NO: 56)
CAGTCTGTGCTGACTCAGCCGCCCTCAGTGTCTGGGGCCCCAGGGCAGAGGGTCACCATCTCCT

GCACTGGGGGCAACTCCAACATCGGGGCAGGTTATCATGTACATTGGTACCAGCAACTTCCAGG

AGCAGCCCCCAAACTCCTCATCTATGGTGACACTAATCGGCCCTCAGGGGTCCCTGACCGATTC

TCTGGCTCTCAGTCTGGCACCTCAGCCTCCCTGGCCATCACTGGGCTCCAGGCTGACGATGAGG

CTGATTATTACTGCCAGTCCTATGACAGAAGCCGGGGTGGTTGGTTTTTCGGCGGAGGGACCCA

GCTGACCGTCCTA

>hLept5_HCv
(SEQ ID NO: 57)
CAGGTGAAGCTGGTGGAGTGGTCGCTGAGCGTGGTCCAGCCTGGGAGGTCCCTGAGACTCTCCT

GCGCAGCCTCTGGATTCACCTTCAGTAGCTATGCTATGCACTGGGTCCGCCAGGCTCCAGGCAA

GGGGCTGGAGTGGGTGGCAGTTATATCATATGATGGAAGCAATAAATACTACGCAGACTCCGTG

APPENDIX I-continued

Variable DNA sequences of anti-leptin antibodies

AAGGGCCGATTCACCATCTCCAGAGACAATTCCAAGAACACGCTGTATCTGCAAATGAACAGCC

TGAGAGCTGAGGACACGGCTGTGTATTACTGTGCGAGAGGTCGTGAATACTACTACTACATGGA

CGTCTGGGGCAAAGGGACCACGGTCAGCGTCTCCTCA

>hLept5_LCv (SEQ ID NO: 58)

CAGTCTGTGCTGACTCAGCCACCCTCAGTGTCAGTGGCCCCAGGAAAGACGGCCAGGATTACAT

GTGGGGGATACAACATTGCAAGAAAAAGTGTGCACTGGTACCAGCAGAAGCCAGGCCAGGCCCC

TGTGTTGGTCATGTATAATGATAACGACCGGCCCTCAGGGATCCCTGAGCGATTCTCTGGCTCC

AACTCTGGGAACACGGCCACCCTGACCATCAGCAGGGTCGAAGCCGGGGATGAGGCCGACTATT

ACTGTCAGGTGTGGGATAATAGTGATTATGTCTTCGGAACTGGGACCAAGGTCACCGTCCTA

>hLept6_HCv (SEQ ID NO: 59)

CAGGTGCAGTTGATGCAGTCTGGGGCTGAGGTGAAGAAGCCTGGGGCCTCAGTGAAGGTTTCCT

GCAAGGCATCTGGATACACCTTCACCAGCTACTATATGCACTGGGTGCGACAGGCCCCTGGACA

AGGGCTTGAGTGGATGGGAATAATCAACCCTAGTGGTGGTAGCACAAGCTACGCACAGAAGTTC

CAGGGCAGAGTCACCATGACCAGGGACACGTCCACGAGCACAGTCTACATGGAGCTGAGCAGCC

TGAGATCTGAGGACACGGCCGTGTATTACTGTGCGAGAGGATTCGGCTACGGTGGTAAGGCCCT

TGACTACTGGGGCCAGGGAACCACGGTCACCGTCTCTTCA

>hLept6_LCv (SEQ ID NO: 60)

GACATCCAGATGACCCAGTCTCCTCCCACCCTGTCTGCATCTGTAGGGGACAGAGTCACCATCA

CTTGCCGGGCCAGTCAGAATATTAATAGTAGGTTGGCCTGGTATCAGCAGAAACCAGGGAGAGC

CCCTAAACTCCTGATCTATAAGGCGTCTACTTTAGAGAGTGGGGTCCCATCGAGGTTCAGCGGC

AGTGGATCTGGGACAGAATTCACTCTCACCATCAGCAGCCTGCAGCCAGATGACTTTGCAACTT

ATTACTGCCAACAGTTTGATAAATATTCGATCACTTTCGGCGGAGGGACCAAGATGGAGATCAA

A

APPENDIX II

Variable amino acid sequences of anti-leptin antibodies

>hLept1_HCv_AA (SEQ ID NO: 61)

QVQLQQLGPGLVKPSETLSLTCNVSGGSVSRGSHYWTWIRQPPGKGLEWI

GYIHTDGSTNFNPSLKSRVTMSLDRSRNQFSLTLSSVTATDTAVYYCARE

PGGALNFWGQGTLVTVSS

>hLept1_LCv_AA (SEQ ID NO: 62)

DFMLTQPPSTSGTPGQRVTISCSGSSSNIGSNTVNWYQQLPGTAPKLLIY

SNNQRPSGVPDRFSGSKSGTSASLAISGLQSEDEADYYCASWDDSLNGVV

FGGGTTVTVL

>hLept2_HCv_AA (SEQ ID NO: 63)

QVQLVQSGAEVKKPGASVKVSCKASGYTFTGYYMHWVRQAPGQGLEWMGR

INPNSGGTNYAQKFQGRVTMTRDTSISTAYMELSRLRSDDTAVYYCASGK

TYYDFWSGGRRGMDVWGQGTMVTVSS

APPENDIX II-continued

Variable amino acid sequences of anti-leptin antibodies

>hLept2_LCv_AA (SEQ ID NO: 64)

DIQLTQSPSSLSASVGDRVTITCRAGQSVSRYLNWFQQKPGKAPKLLIYT

SSNLQSGVPSRFSASGSGTDFTLTISSLQPEDFATYYCQQTYSTPWTFGQ

GTKLEIK

>hLept3_HCv_AA (SEQ ID NO: 65)

QVQLVQSGAEVKKPGSSVKVSCKASGGTFSSYAISWVRQAPGQGLEWMGG

IIPIFGTANYAQKFQGRVTITADESTSTAYMELSSLRSEDTAVYYCARSQ

VPSSYYYGMDVWGQGTMVTVSS

>hLept3_HCv_AA (SEQ ID NO: 66)

QSVLTQPPSVSGAPGQRVTISCTGGNSNIGAGYHVHWYQQLPGAAPKLLI

YGDTNRPSGVPDRFSGSQSGTSASLAITGLQADDEADYYCQSYDRSRGGW

FFGGGTQLTVL

APPENDIX II-continued

Variable amino acid sequences
of anti-leptin antibodies

>hLept5_HCv_AA
(SEQ ID NO: 67)
QVKLVEWSLSVVQPGRSLRLSCAASGFTFSSYAMHWVRQAPGKGLEWVAV

ISYDGSNKYYADSVKGRFTISRDNSKNTLYLQMNSLRAEDTAVYYCARGR

EYYYYMDVWGKGTTVSVSS

>hLept5_LCv_AA
(SEQ ID NO: 68)
QSVLTQPPSVSVAPGKTARITCGGYNIARKSVHWYQQKPGQAPVLVMYND

NDRPSGIPERFSGSNSGNTATLTISRVEAGDEADYYCQVWDNSDYVFGTG

TKVTVL

APPENDIX II-continued

Variable amino acid sequences
of anti-leptin antibodies

>hLept6_HCv_AA
(SEQ ID NO: 69)
QVQLMQSGAEVKKPGASVKVSCKASGYTFTSYYMHWVRQAPGQGLEWMGI

INPSGGSTSYAQKFQGRVTMTRDTSTSTVYMELSSLRSEDTAVYYCARGF

GYGGKALDYWGQGTTVTVSS

>hLept6_LCv_AA
(SEQ ID NO: 70)
DIQMTQSPPTLSASVGDRVTITCRASQNINSRLAWYQQKPGRAPKLLIYK

ASTLESGVPSRFSGSGSGTEFTLTISSLQPDDFATYYCQQFDKYSITFGG

GTKMEIK

What is claimed is:

1. An isolated antibody designated hLept1 that binds human leptin and comprises V$_H$ CDR1, CDR2 and CDR3 sequences: GGSVSRGSHY (SEQ ID NO:1), IHTDGST (SEQ ID NO:2), and AREPGGALNF (SEQ ID NO:3), and V$_L$ CDR1, CDR2 and CDR3 sequences: SSNIGSNT (SEQ ID NO:16), SNN, and ASWDDSLNGVV (SEQ ID NO:17).

2. The antibody of claim 1 comprising the V$_H$ and V$_L$ sequences:

(SEQ ID NO: 61)
QVQLQQLGPGLVKPSETLSLTCNVSGGSVSRGSHYWTIRQPPGKGLEWI

GYIHTDGSTNFNPSLKSRVTMSLDRSRNQFSLTLSSVTATDTAVYYCARE

PGGALNFWGQGTLVTVSS and (SEQ ID NO: 62)
DFMLTQPPSTSGTPGQRVTISCSGSSSNIGSNTVNWYQQLPGTAPKLLIY

SNNQRPSGVPDRFSGSKSGTSASLAISGLQSEDEADYYCASWDDSLNGVV

FGGGTTVTVL.

3. The antibody of claim 1 that is a humanized monoclonal IgG antibody.

4. A method of reducing leptin levels in a human subject, comprising administering an effective amount of the antibody of claim 1 to said subject.

* * * * *